(12) United States Patent
Chacon

(10) Patent No.: US 7,414,077 B2
(45) Date of Patent: Aug. 19, 2008

(54) THERAPEUTIC INTERVENTION TO MIMIC THE EFFECT OF CALORIC RESTRICTION

(76) Inventor: Marco Chacon, 702 Edgehill Dr., Bel Air, MD (US) 21014

( * ) Notice: Subject to any disclaimer, the term of this patent is extended or adjusted under 35 U.S.C. 154(b) by 0 days.

(21) Appl. No.: 10/120,362

(22) Filed: Apr. 12, 2002

(65) Prior Publication Data

US 2002/0173450 A1 Nov. 21, 2002

Related U.S. Application Data

(63) Continuation of application No. PCT/US00/28322, filed on Oct. 13, 2000.

(60) Provisional application No. 60/159,099, filed on Oct. 13, 1999.

(51) Int. Cl.
A61K 31/202 (2006.01)
A61K 31/22 (2006.01)
A61K 31/20 (2006.01)

(52) U.S. Cl. .................... 514/560; 514/563; 514/564; 514/546

(58) Field of Classification Search ................. 514/560, 514/563, 564, 546
See application file for complete search history.

(56) References Cited

U.S. PATENT DOCUMENTS

| | | | | |
|---|---|---|---|---|
| 4,752,618 A | * | 6/1988 | Mascioli et al. | 514/549 |
| 4,826,877 A | * | 5/1989 | Stewart et al. | 514/560 |
| 4,871,768 A | * | 10/1989 | Bistrian et al. | 514/547 |
| 4,879,312 A | * | 11/1989 | Kamarei et al. | 514/560 |
| 5,043,328 A | * | 8/1991 | Weithmann | 514/78 |
| 5,164,414 A | * | 11/1992 | Vincent et al. | 514/563 |
| 5,221,668 A | * | 6/1993 | Henningfield et al. | 514/23 |
| 5,223,285 A | * | 6/1993 | DeMichele et al. | 426/72 |
| 5,231,085 A | * | 7/1993 | Alexander et al. | 514/44 |
| 5,260,336 A | * | 11/1993 | Forse et al. | 514/560 |
| 5,397,701 A | * | 3/1995 | Devadas et al. | 435/68.1 |
| 5,541,225 A | * | 7/1996 | Leaf et al. | 514/560 |
| 5,571,689 A | * | 11/1996 | Heuckeroth et al. | 435/68.1 |
| 5,709,863 A | | 1/1998 | Pageat | |
| 5,731,346 A | | 3/1998 | Egberg | |
| 5,747,533 A | * | 5/1998 | Egberg et al. | 514/549 |
| 5,767,156 A | | 6/1998 | Ferrante | |
| 5,780,237 A | * | 7/1998 | Bursten et al. | 435/7.1 |
| 5,871,954 A | * | 2/1999 | Heuckeroth et al. | 435/68.1 |
| 6,034,132 A | | 3/2000 | Remmereit | |
| 6,036,992 A | * | 3/2000 | Borror et al. | 426/662 |
| 6,054,481 A | | 4/2000 | Pageat | |
| 6,077,867 A | | 6/2000 | Pageat | |
| 6,169,113 B1 | * | 1/2001 | Pageat | 514/558 |
| 6,365,628 B1 | * | 4/2002 | Berge | 514/546 |
| 6,380,253 B1 | * | 4/2002 | Das | 514/560 |
| 6,384,252 B1 | | 5/2002 | Pageat | |
| 6,395,782 B1 | * | 5/2002 | Cook et al. | 514/560 |
| 6,441,036 B1 | * | 8/2002 | Berge | 514/552 |

FOREIGN PATENT DOCUMENTS

| | | | |
|---|---|---|---|
| CA | 2 318 392 | | 7/1999 |
| EP | 0071357 | | 2/1983 |
| EP | 0635267 | | 1/1995 |
| JP | 60-025934 | * | 8/1985 |
| JP | 03-297364 | | 12/1991 |
| JP | 07267864 | | 10/1995 |
| WO | WO9312756 | | 7/1993 |
| WO | WO 98/16215 A1 | * | 4/1998 |
| WO | WO 01/17524 A1 | * | 3/2001 |

OTHER PUBLICATIONS

Weindruch, R., "Caloric Restriction and Aging", Scientific American, 46-52 (1996).
Roth, G., et al.; "Effect of Caloric Modification on Aging Rate in Nonhuman Primates: A Progress Report", Proceedings of an International Conference sponsored by the American Health Foundation, 193-204 (1988).
Masoro, E., et al.; "Caloric Restriction and Aging in Rats", Proceedings of an International Conference sponsored by the American Health Foundation, 123-136 (1988).
Weindruch, R.; "Retardation of Aging by Caloric Restriction in Mice"; Proceedings of an International Conference sponsored by the American Health Foundation,109-121 (1988).
Fernandes, G., "Modulation of Immune Functions and Aging by Omega-3 Fatty Acids and/or Calorie Restriction", Proceedings of an International Conference sponsored by the American Health Foundation, 263-287 (1988).
Tollotson, J., et al.; "Effects of Linoleic acid on mammary tumor cell proliferation are associated with changes in p53 protein expression" International Journal of Oncology, vol. 3, 81-87 (1993).
Johannes, L.; "The Surprising Rise of a Radical Diet: 'Calorie Restriction'", The Wall Street Journal, vol. CCXXXIX, A1 & A10 (2002).
Wiersinga, W., et al.; "Inhibition of nuclear T3 binding by fatty acids: dependence on chain length, unsaturated bonds, cis-trans configuration and esterification", Int. J. Biochem, vol. 3, 269-273 (1990) (Abstract only).
Inoue, A. et al.; "Nuclear Receptor Solubilized Receptor and the Receptor in Cultured Cells", Eur J Biochem, vol. 183, 565-572 (1989) (Abstract only).

(Continued)

*Primary Examiner*—Brian-Yong S Kwon
(74) *Attorney, Agent, or Firm*—Hunton & Williams LLP

(57) ABSTRACT

Methods are provided for promoting longevity and decreasing the incidence of ageing associated pathologies (e.g. cancer) by the administration of one or more of the following LFFA: linoleic, oleic, and palmitic acid. Secondary LFFA derived from this set, as well as their CoA derivatives and synthetic analogs, are effective also in promoting longevity and delaying the onset of age associated disorders. In addition, interventions including LFFA and CoA LFFA formulations are described which protect the organism from acute physical stress, tissue damage, and hypoxia, either due to trauma or secondary to surgical procedures.

3 Claims, 4 Drawing Sheets

OTHER PUBLICATIONS

Davis, F. B., et al.; "Action of Long-Chain Fatty Acids in-Vitro on Calcium-Stimulatable Magnesium-Dependent Atpase Activity in Human Red Cell Membranes", Biochem J, vol. 248, 511-516, (1987) (Abstract only).

Lane, M., et al.; "The Serious Search for an Anti-Aging Pill", Scientific American, 36-41, (2002).

Liepa, G., et al.; Food restriction as a modulator of age-related changes in serum lipids, The American Physiological Society, vol. 80, 253-257, (1980).

Roth, G., et al., Slowing ageing by caloric restriction, Nature Medicine, vol. 1, 414-415, (1995).

Pande et al, "Protective role of adenine nucleotide translocase in $O_2$-deficient hearts," American Journal of Physiology—Heart and Circulatory Physiology, 1984, U.S., vol. 16, No. 1, pp. H25-H34.

Database WPI, Section Ch, Week 199207, Derwent Publications Ltd., London, GB, AN 1992-053592, XP002299804 & JP 03 297364 A (Nippon Oils & Fats Co Ltd.), Dec. 27, 1991, Abstract.

Database WPI, Section Ch, Week 198726 Derwent Publications Ltd., London, GB, AN 1987-180578, XP002299805 & JP 62 108844 A (Tsumura Juntendo KK) May 20, 1987, Abstract.

Database WPI, Section Ch, Week 199716 Derwent Publications Ltd., London, GB, AN 1997-119450, XP002299806 & CN 1 080 131 A (Wang R) Jan. 5, 1994, Abstract.

Patent Abstracts of Japan, vol. 2000, No. 11, Jan. 3, 2001, & JP 2000 212058 A (Maruzen Pharmaceut Co Ltd), Aug. 2, 2000, Abstract.

Blonk, MC, et al., "Dose-response effects of fish oil supplementation to healthy volunteers," Am. J. Clin. Nutr. 52(1); 120-127, 1990.

Bregenard, C. et al., "The influence of free fatty acids on the free fraction of thyroid hormones in serum as estimated by ultrafiltration." Acta Endocrinol. 116(1):102-107, 1987.

El Boustani, et al., "Enteral absorption in man of eicosapentaenoic acid in different chemical forms," Lipids 22(10):711-714, 1997.

Goodman, MN, "Starvation in the rat. II. Effect of age and obesity on protein sparing fuel metabolism," Am J. Physiol. Oct; 239(4):E277-E286, 1980.

Hayashi, T. et al., "Stimulation of cell proliferation and inhibition of gap junctional intercellular communication by linoleic acid," Cancer Lett. 112(21):103-11, 1997.

Ikeda, I. et al. "Digestion and lymphatic transport of eicosapentaenoic and docosahexaenoic acids given in the form of triacylglycerol, free acid and ethyl ester in rats," Biochem Biophys Acta 1259(3):297-304, 1995.

Leaf, A. et al., "Do fish oils prevent restenosis after coronary angioplasty?" Circulation 90(5):2248-2257, 1994.

Robinson, D.R. et al., "Suppression of autoimmune disease by dietary n-3 fatty acids," J. Lipid Res. 34(8): 1435-1444, 1993.

Swarts, HG, et al., "Binding of unsaturated fatty acids to Na+, K(+)-ATPase leading to inhibition and inactivation," Biochim. Biophys Acta 1024:32-40, 1990.

Tremoli, E. et al., "Prolonged inhibition of platelet aggregation after n-3 fatty acid ethyl ester ingestion by healthy volunteers," Am J. Clin. Nutr. 61(3):607-613, 1995.

Tillotson, et al. (1993) "Effects of linoleic acid on mammary tumor cell proliferation are associated with changes in p53 protein expression." *International Journal of Oncology* 3(1): 81-87.

Zusman, Comparative anticancer effects of vaccination and dietary factors on experimentally-induced cancers, In Vivo 12: 675-690 (1998).

Axelrod et al., Stress hormones: Their interaction and regulation, Science, vol. 224, pp. 452-459, May 1984.

Chopra et al., Relationship between serum free fatty acids and thyroid hormone binding inhibitor in nonthyroid illnesses, Journal of Clinical Endocrinology and Metabolism, vol. 60, No. 5, pp. 980-984, 1985.

Kelly et al., Indetification of nak-atpase inhibitors in human plasma as nonesterified fatty acids and lysophospholipids, The Journal of Biological Chemistry, vol. 261, No. 25, Issue of Sep. 5, pp. 11704-11711, 1986.

Rose, D.P., Dietary Fat, Fatty Acids and Breast Cancer, Breast Cancer, Mar. 25, 1997;4(1):7-16.

Miles et al., Glucose and ketone body kinetics in diabetic ketoacidosis, Clinics in Endocrinology and Metabolism, vol. 12, No. 2, Jul. 1983, pp. 303-319.

Berridge et al., Calcium- a life and death signal, Nature, vol. 395, Oct. 15, 1998, pp. 645-648.

Bonventre, Mediators of ischemic renal injury, Ann. Rev. Med. 1988, 39: 531-545.

Cahill, Starvation in man, Clinics in Endocrinology and Metabolism, vol. 5, No. 2, Jul. 1976, pp. 397-415.

Chopra et al., Evidence for an inhibitor of extrathyroidal conversion of thyroxine to 3, 5, 3'-triiodothyronine in sera of patients with nonthyroidal illnesses, Journal of Clinical Endocrinology and Metabolism, vol. 60, No. 4, pp. 666-672, 1985.

Chopra et al., A competitive ligand binding assay for measurement of thyroid hormone-binding inhibitor in serum and tissues, Journal of Clinical Endocrinology and Metabolism, vol. 58, No. 4, pp. 619-628, 1985.

Pardee, $G_1$ events and regulation of cell proliferation, Science, vol. 246, pp. 603-608, Nov. 3, 1989.

Li, et al., Fatty acyl-co-as are potent inhibitors of the nuclear thyroid hormone receptor in vitro, J. Biochem, vol. 107, No. 5, pp. 699-702 (1990).

Li et al., Fatty acyl-coa binding activity of the nuclear thyroid hormone receptor, Journal of Cellular Biochemistry, vol. 51, pp. 458-464 1993.

Norbeck et al., Fatty acid composition of serum and adipose tissue lipids in males with chronic renal failure, Acta Med. Scand., vol. 211, pp. 75-85, 1982.

Opstad et al., The thyroid function in young men during prolonged exercise and the effect of energy and sleep deprivation, Clinical Endocrinology (1984), 20, pp. 657-669.

Patterson et al., Store-operated $Ca^{2+}$ entry: Evidence for a secretion-loke coupling model, Cell., vol. 98, pp. 487-499, Aug. 20, 1999.

Perkins et al., Chemoprevention of spontaneous tumorigenesis in nullizygous p53-deficient mice by dehydroepiandrosterone and its analog 16α-fluoro-5androsten-17-one, Carcinogenesis, vol. 18, No. 5, pp. 989-994, 1997.

Passaniti et al., Methods in laboratory investigation, A simple, quantitive method for assessing angiogenesis and antiangiogenic agents using reconstituted basement membrane, heparin, and fibroblast growth factor, Laboratory Investigation, vol. 67, No. 4, pp. 519-528, 1992.

Girard et al., Ketone-body metabolism during the neonatal period, Biochemical Society Transactions, vol. 9, pp. 344-345, 1981.

Haddad et al., Hypoxia and respiratory control in early life, Ann. Rev. Physiol., 1984, 46:629-643.

Van Der Klis et al., Competitive inhibition of t3 binding to $α_1$ thyroid hormone receptors by fatty acids, Biochemical and Biophysical Research Communications, vol. 179, No. 2, 1991, Sep. 16, 1991, pp. 1011-1016.

Hochachka, Defense strategies against hypoxia and hypothermia, Science, vol. 231, pp. 234-241, 1986.

Heydari et al., Does gene expression play any role in the mechanism of the anitaging effect of dietary restriction?, Annals N.Y. Academy Science 663, pp. 384-395, 1992.

Lefebvre et al., Muscular exercise and pancreatic function in rats, Israel J. Med. Science, vol. 8, No. 3, Mar. 1972, pp. 390-398.

Maclennan et al., Structure-function relationships in sarcoplasmic or endoplasmic reticulum type $Ca^{2+}$pumps[a], Annals N.Y. Academy Science 671, pp. 1-10, 1992.

Lee et al., Gene expression profile pf aging and its retardation by caloric restriction, Science, vol. 285, Aug. 27, 1999, pp. 1390-1393.

Lane et al., Calorie restriction lowers body temperature in rhesus monkeys, consistenmt with a postulated anti-aging mechanism in rodents, Proc. Natl., Acad. Sci., vol. 93, pp. 4159-4164, Apr. 1996.

O'Connell et al., Changes in serum concentrations of 3, 5, 3'-triiodothyronine and 3, 5, 3'-triiodothyronine during prolonged moderate exercise, Journal of Clinical Endocrinology and Metabolism, vol. 49, No. 2, pp. 242-246, 1979.

Laskey et al., S phase of the cell cycle, Science, vol. 246, Nov. 3, 1989, pp. 609-614.

Wartofsky et al., Alterations in thyroid function in patients with systemic illness: the "euthyroid sick syndrome", Endocrine Reviews, vol. 3, No. 2, pp. 164-217, 1982.

Wang et al., Comparative dose-dependence study of fk506 and cyclosporin a on the rate of axonal regeneration in the rat sciatic nerve, The Journal of Pharmacology and Experimental Therapeutics, vol. 282, No. 2, pp. 1084-1093, 1997.

Fain et al., Hormonal regulation of lipoysis: Role of cyclic nucleotides adenosine, and free fatty acids, Advances in Experimental Medicine and Biology, pp. 43-77. 1976.

Waldron et al., Endoplasmic reticulum calcium pump expression and control of cell growth, The Journal of Biological Chemistry, vol. 269, No. 16, Issue Apr. 22, pp. 11927-11933, 1994.

Vagenakis et al., Diversion of peripheral thyroxine metabolism from activating to inactivating pathways during complete fasting, J. Clin. Endocrinal Metab. 41: 191-194, 1975.

Seitz et al., Rapid conversion by insulin of hepatic intermediary metabolism from glucose production to glucose utilization in the liver of alloxan-diabetic rats, Diabetes 26: 1159-1174, 1977.

Rys-Sikora et al., Modification of gtp-activated calcium translocation by fatty acyl-coa esters, The Journal of Biological Chemistry, vol. 269, No. 50, Issue of Dec. 16, pp. 31607-31613, 1994.

Bora et al., Myocardial cell damage by fatty acid ethyl esters, Journal of Cardiovascular Pharmacology, vol. 27, No. 1, 1996, pp. 1-6.

Lange et al., Mitochondrial dysfunction induced by fatty acid ethyl esters, myocardial metabolites of ethanol, J. Clin. Invest., vol. 72, Aug. 1983, pp. 724-731.

Kuratko et al., Linoleic acid and tumor necrosis factor-$\alpha$ increase manganese superoxide dismutase activity in intestinal cells, Cancer Letters 130, 1998, pp. 191-196.

Zusman et al., Tumor-promoting and tumor-protective effects of high-fat diets on chemically induced mammary cancer rats, Anticancer Research 17:349-356, 1997.

Rose et al., Dietary fatty acids and breast cancer invasion and metastasis, Nutrition and Cancer, vol. 21, No. 2, pp. 103-111, 1994.

Weindruch et al., Influence of controlled dietary restriction on immunologic function and aging, Fed. Proc., vol. 38, No. 6, May 1979, pp. 2007-2016.

Graber et al., $Ca^{2+}$ pools and cell growth: Arachidonic acid induces recovery of cells growth-arrested by $Ca^{2+}$ pool depletion, The Journal of Biological Chemistry, vol. 271, No. 2, Issue of Jan. 12, pp. 883-888, 1996.

Portnay et al., The effect of starvation on the concentration and binding of thyroxine and triiodothyronine in serum and on the response to trh, J. Clin. Endocrinol Metab. 39:199, 1974, pp. 191-194.

Helenius et al., Abnormal thyroid function test in severe non-thyroidal illness: diagnostic and pathphysiologic aspects, Scand. J. Clin. Lab. Invest., 39, pp. 389-397, 1979.

Flink et al., Alterations of long-chain free fatty acid and magnesium concentrations in acute myocardial infarction, Arch. Intern. Med., vol. 141, Mar. 1981, pp. 441-443.

Wiersinga et al., Inhibition of nuclear $T_3$ binding by fatty acids, Metabolism, vol. 37, No. 10 (Oct. 1988), pp. 996-1002.

Williamson et al., Strategies for the supply of lipid substrates during post-natal brain development: A tale of two tissues, Dev. Neurosci. 1993; 15: 156-164.

Hursting et al., Calorie restriction delays spontaneous tumorigenesis in p 53-knockout transgenic mice, Proc. Natl. Acad. Sci., vol. 91, pp. 7036-7040, Jul. 1994.

Granot et al., Patterns of glucose intolerance and free fatty acid behavior in viral hepatitis, Israel J. Med. Sci., vol. 17, 1981, pp. 12-18.

* cited by examiner

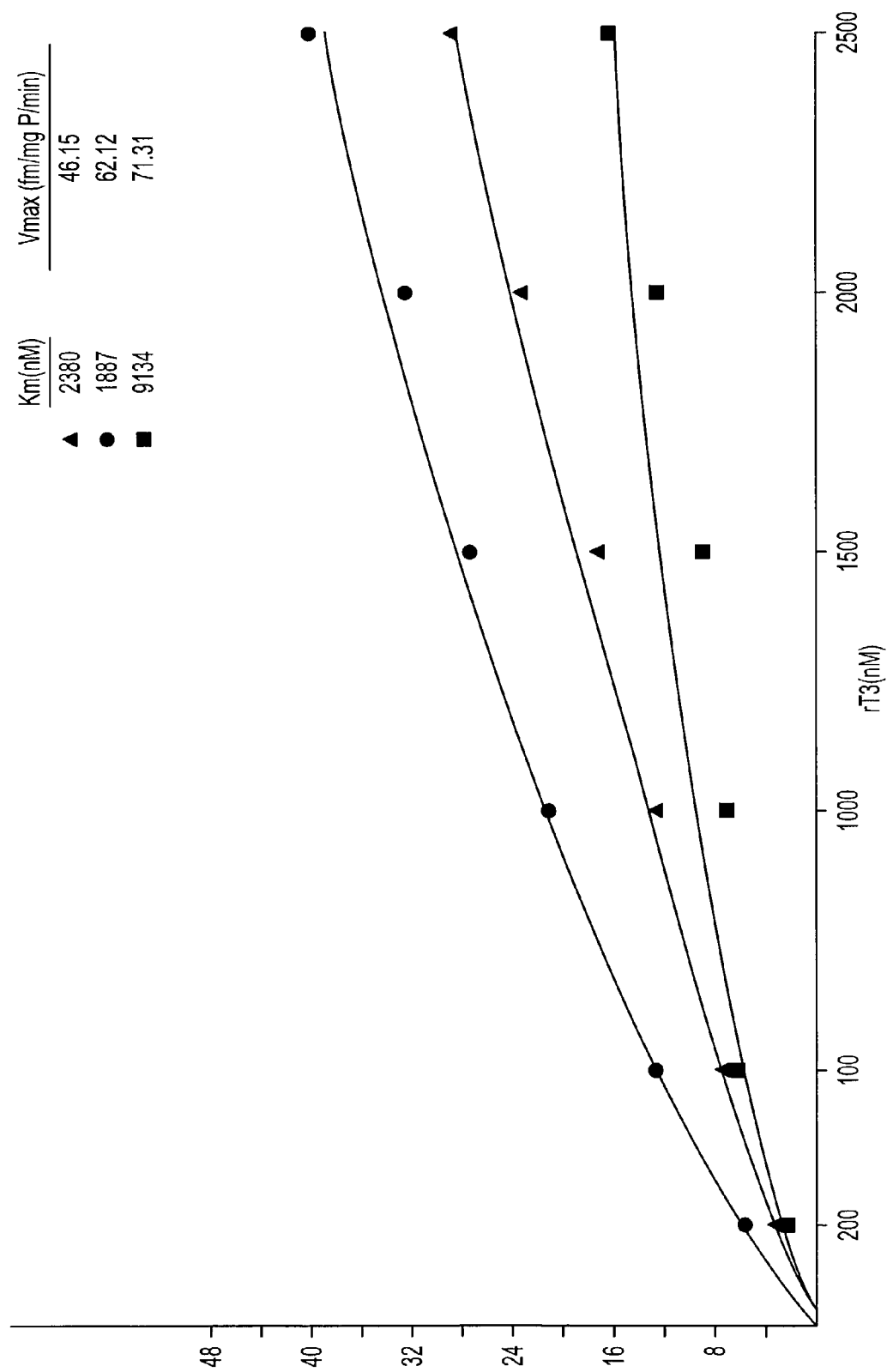

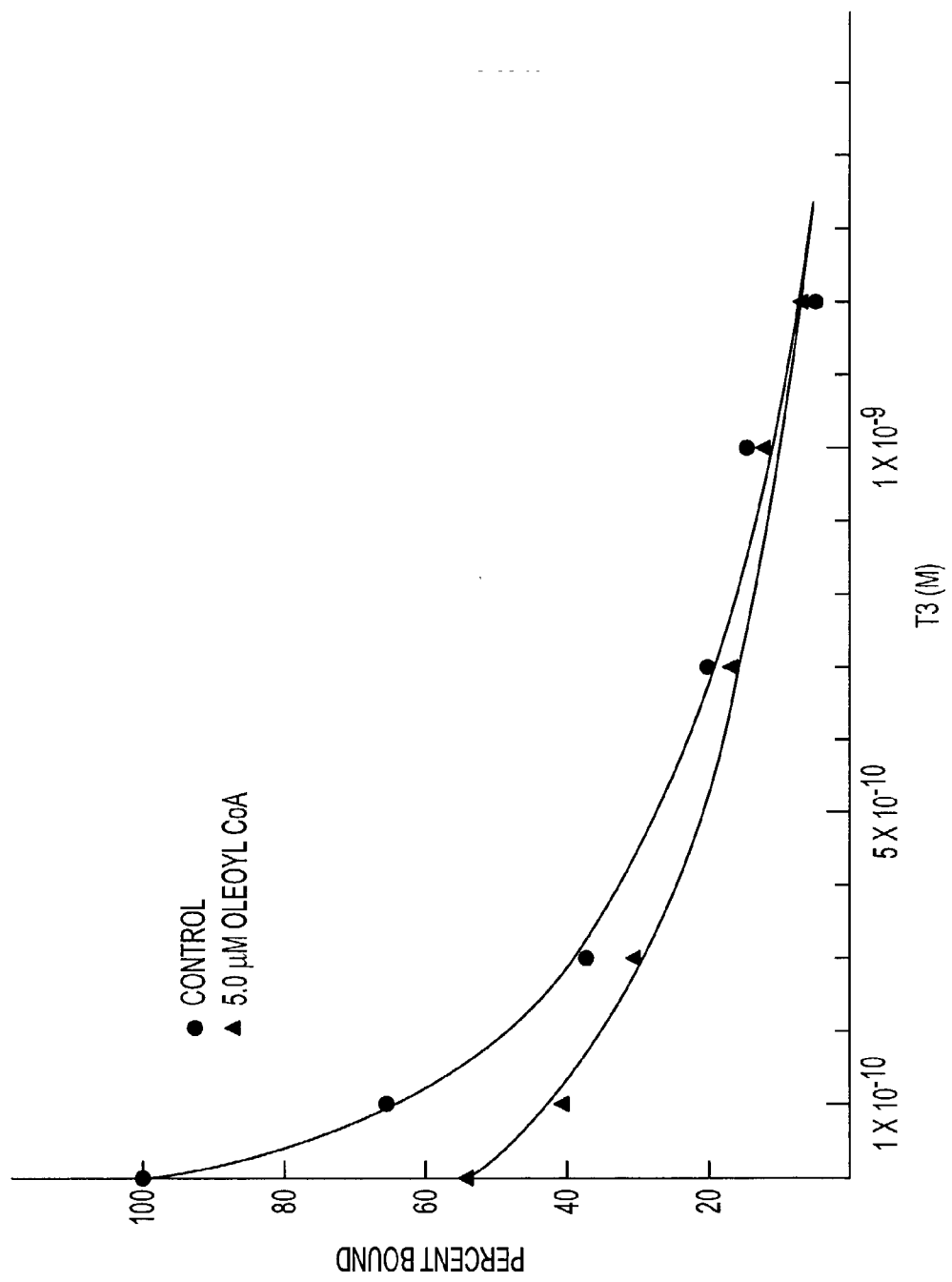

THERAPEUTIC INTERVENTION TO MIMIC THE EFFECT OF CALORIC RESTRICTION

CROSS-REFERENCE TO RELATED APPLICATION

This application is a continuation of PCT/US00/28322, filed Oct. 13, 2000, which claims priority to U.S. Application No. 60/159,099, filed Oct. 13, 1999.

BACKGROUND OF THE INVENTION

1. Field of the Invention

This invention is directed to methods for increased longevity, delay of aging associated disorders, protection from acute physical stress and induction of regeneration and healing by administration of Long chain Free Fatty Acids (LFFA) and CoA derivatives of Long chain Free Fatty Acids (CoALFFA) in mammals.

2. Review of Related Art

Sixty years of active investigation has conclusively demonstrated that reduced caloric intake extends life span in a wide variety of animal species, including mammals (e.g., mice and rats) (Ingram, D. K. et al., "The Potential for Nutritional Modulation of the Aging Process," *Food and Nutrition Press* (1991)). Moreover, the incidence of pathologies associated with aging in rodents are also delayed by caloric restriction (CR) (Roth, G. S. et al., *Nature Medicine* 1:414-415 (1995) and Weindruch, R., Scientific American: 46-52 (January 1996)) More recently, on-going CR studies using primates seem to mimic comparable biochemical changes observed in rodents (Roth, et al., 1995), and, by extension, the same effects should be expected to occur in humans subjected to caloric restriction.

Several hypotheses have been proposed to explain the mechanism(s) underlying the beneficial effects of CR, and some of these have been discarded. Today, it is accepted that the anti-aging effects of CR are not mediated by a retardation in growth and development, or by a reduction in body fat of animals subjected to caloric restriction. Still under investigation is the hypothesis that the beneficial effects of CR are due to a reduction in oxidative damage secondary to the generation of oxygen radicals (Weindruch, R., 1996). Support for this hypothesis is derived from studies demonstrating a reduction in lipid peroxidation and induction of the enzyme Superoxide Dismutase (Heydari, A. R. et al., *Annals N.Y. Academy Science* 663-384-395 (1992) and Yu, B. P., "Free Radicals in Aging" *CRC Press* (1993)) in animals subjected to caloric restriction. Another hypothesis that has received considerable attention attributes the beneficial effects of CR to the induction of "protective genes". Investigators pursuing this hypothesis have demonstrated the induction of genes coding for SOD, HRP-70 and A2u-globulin and concluded that the effects of CR regulate gene expression at the transcriptional level (Heydari, A. R. et al., (1992). Most recently, using a genomics based approach to analyze gene expression in the skeletal muscles of aged and CR mice, it was proposed that CR retards the aging process by causing a metabolic shift resulting in increased protein turnover and decreased macromolecular damage (Lee, et al., 1999, *Science*, 285:1390-1393).

Although it is likely that protection against oxidative damage, and the induction of protective genes may play a role in the beneficial effects of CR, the underlying mechanism(s) involved remain a mystery.

SUMMARY OF THE INVENTION

This invention provides a method for improving the health of a mammal comprising administering to the mammal a composition comprising LFFA, CoALFFA, or other LFFA analogs in an amount sufficient to (a) inhibit thyroid hormone receptor binding in vivo, (b) inhibit Na/K ATPase and Ca ATPase in vivo, (c) conserve energy fuels, (d) reduce oxygen consumption in vivo, (e) cause a decrease in core body temperature in said mammal, and/or (f) activation of protective genes in vivo. The protective genes include p53, SOD, $\alpha$-2-globulin, and/or HSP-70. Suitable-mammals include livestock, household pets, and especially humans. Preferred analogs of LFFA have enhanced half-lives in the circulation in the mammal. In preferred embodiments of this method, angiogenesis in the mammal is decreased, and/or hypoxia tolerance in the mammal is enhanced. This invention also provides compositions comprising LFFA, CoALFFA, or other LFFA analogs formulated for administering according to the method of this invention.

In one embodiment of this invention, the method comprises administering LFFA, CoALFFA, or other LFFA analogs to a human anticipating surgery, and the administration is carried out prior to surgery. In an alternative embodiment, the method comprises administering LFFA, CoALFFA, or other LFFA analogs to a mammal suffering from a condition characterized by hypoxia or an increased risk of local or systemic hypoxia.

BRIEF DESCRIPTION OF THE DRAWINGS

FIGS. 2A and 2B show that LFFAs inhibit thyroid hormone synthesis in vitro, as shown by the effect of in vitro free fatty acids on 5' deiodinase activity as a function of substrate concentration. Reaction velocities were measured under control conditions (▲) and in the presence of 1 mM free fatty acids palmitic acid (●) and oleic acid (■). Each point on the curve represents the mean of triplicate determinations. Lineweaver-Burk plots described lines characterized by $r^2$ from 0.988-0.999.

FIGS. 3A and 3B show that CoA-LFFAs inhibit T3 receptor binding, as demonstrated by the effect of oleoyl CoA on kinetic parameters (dissociation constant, Kd, and maximum binding, MBC). The Kd and MBC were obtained from Scatchard analysis of standard competition experiments in the presence and absence of 5 µM concentrations of oleoyl CoA. Values are the average of duplicate determinations.

DETAILED DESCRIPTION OF THE EMBODIMENTS

Figure 1:
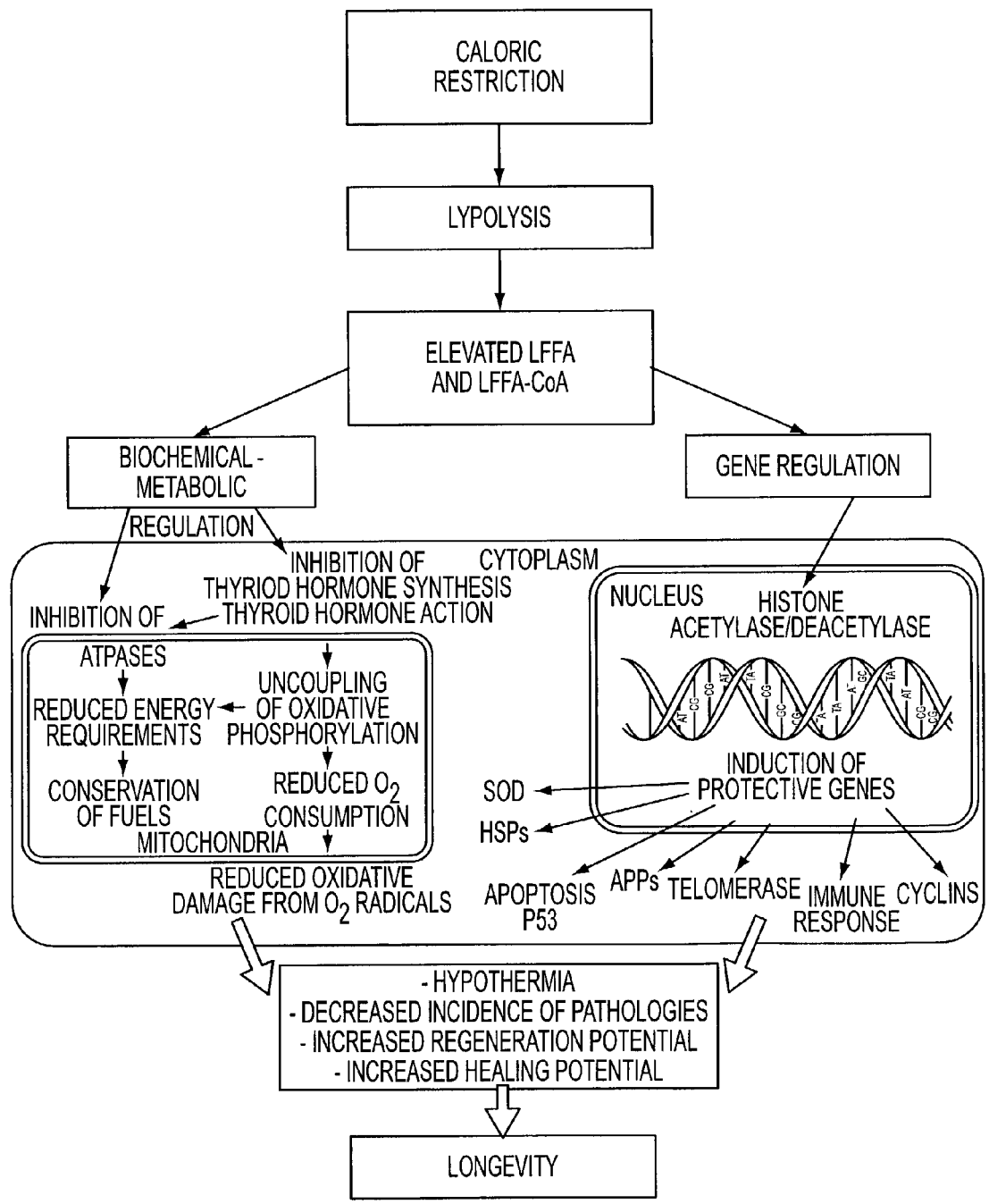
FIG. 1 is a schematic representation of the Single Mediator Hypothesis.

The present invention relates to the use of LFFAs and CoALFFAs, either singly or in combination, to be provided either orally (as dietary supplements) or in pharmaceutical carriers (e.g., as slow-release implantables) to increase life span and to reduce the incidence and/or to delay the onset of pathologies associated with aging. The inventor has discovered that LFFAs and CoALFFAs mediate the increase in life expectancy and the reduction in aging associated disorders observed with caloric restriction in mammals. Moreover, the inventor has established that treatment of ad-libitum fed animals with LFFAs and CoALFFAs increases their life span and reduces the incidence of age associated disorders to rates comparable to those observed in calorie restricted animals. Apparently, LFFAs and CoALFFAs function as stress signals that trigger a stress/protective response, i.e., a series of protective mechanisms including: efficient utilization of alternate fuels, reduction in oxygen consumption, prevention of oxidative tissue damage, induction of heat shock proteins, activation of the cell cycle (promoting tissue regeneration and healing), as well as induction of DNA repair and anti-tumor genes.

Rationale of the Invention

While not wishing to be bound to any particular theory which might limit the scope of the present embodiment, the inventor has developed the following rationale for the present invention to explain and expand the observations. This rationale is based on the definition of CR as a form of mild to moderate starvation. Darwinian principles are the foundation of the logic employed that led to the present invention through the elucidation of metabolic and molecular mechanisms underlying the health benefits associated with CR.

The survival of all species, including the human animal, has depended on the ability to respond quickly to external challenges that compromise the biochemical integrity and life of the organism. In the wild, when a species is threatened by injury, disease or starvation, there is a built-in wisdom in nature that enables the organism to unleash biochemical signals that are involved in the conservation of energy fuels, in mounting an immune response, in cell cycle activation and tissue repair. Assuming a non-lethal event (whether injury, infectious disease or famine), eventually, the affected animal heals, or the disease runs its course, or food becomes plentiful once again, and the organism regains its health. The organism manages to survive in the absence of any medical intervention. Moreover, a benefit (survival and restored health) is harnessed from an apparent deficit. Therefore, against the conventional wisdom, we have to consider the following paradox: It appears that it is during episodes of catabolic stress that an animal is best suited to survive, to regenerate and to heal.

In this context, chronic CR may be perceived by the organism as a threat to its survival. CR is in biochemical terms a catabolic stress which, nonetheless, marshals several positive and protective mechanisms, including: 1) Blocking of thyroid hormone expression with a consequent reduction in oxygen consumption and the formation of harmful oxygen radicals, as well as conservation of energy fuels. 2) Inhibition of high energy ion channels (ATPases). 3) Induction of protective genes generating a powerful immune response. Therefore, the calorie restricted animal is better suited to survive injuries and to recover faster from disease. The net effect is a decrease in the incidence of ailments associated with aging and an overall slow-down of the aging process.

The present invention relates to factors involved in mediating the protective effects of CR, and the inventor's discovery of these factors was based on the premise that such factors would have to be selectively released during catabolic stress (potential candidates therefore included hormones, second messengers, intermediary metabolites, co-factors, etc.). In mammals, the sympatho-adrenal axis is activated in response to injury, disease, or starvation, resulting in the release of stress hormones (glucocorticoids and catecholamines) which together with low insulin-glucagon ratios promote increased levels of cAMP (Axelrod, J. et al., *Science* 224:452-459 (1984)). The resulting metabolic changes are swift and profound. Thyroid hormone levels are decreased, resulting in a condition often referred to as Euthyroid Sick Syndrome, that is, low thyroid hormones in the absence of clinical hypothyroidism (Wartofsky, L. et al., *Endocrine Review* 3:164-217 (1982)). Bioactive proteins (cytokines, lymphokines and growth factors) through complex signal transduction pathways, mediate gene expression resulting in cell cycle activation, tissue regeneration and restored health (Pardee, A. B., *Science* 246:603-608 (1989) and Laskey, R. A. et al., *Science* 246:609-614 (1989)). In view of the nature of CR, the inventor was able to focus on the effects of catabolic stress on energy metabolism. In calorie restriction (as well as during catabolic stress in general), lipolysis, ketogenesis and gluconeogenesis are favored over glycolysis and lipogenesis (Fain, J. M., et al., *Adv. Exper. Med. Biol.* 111:43-77 (1976)). Secondary to β-adrenergic stimuli, elevated levels of cAMP cause an activation of hormone sensitive lipase resulting in an immediate release of specific long chain free fatty acids from depot fat, including: Linoleic, oleic, and palmitic acids. These free fatty acids are increased in the circulation and in tissues where they are readily coupled to Coenzyme A (Seitz, H. J. et al., *Diabetes* 26:1159-1174 (1977)).

Observed Effects of Free Fatty Acids

The inventor has concluded that free fatty acids (LFFA) and/or their CoA derivatives are the factors which mediate the protective effects of CR in vivo for the following reasons: (see FIG. 1)

1) Increased levels of FREE FATTY ACIDS and their CoA DERIVATIVES due to lipolysis are a common denominator in catabolic stress (Granot, C. et al., *Isr. J. Med. Sci.* 17:12 (1981); Flink, E. B. et al., *Arch. Intern. Med.* 141:441 (1981); Norbeck, H. E. et al., *Acta. Med. Scand.* 211:75 (1982); Helenius, T. et al., *Scan J. Clin. Lab. Invest.* 39:398; and Miles, J. M. et al., *Clinics in Endocrin. and Metab*. Saunders, Pa., vol. 12:303 (1983)). Moreover, mild to moderate starvation is also accompanied by increased levels of free fatty acids (Cahill, G. F., *Clinics in Endocrin. and Metab.* 5:397-415 (1976)). Most compelling is the fact that specific LFFAs (oleic, linoleic and palmitic acids) are elevated in calorie restricted rats (Liepa, G. U. et al., *Am. J. Phys.* 238:E253-E257 (1980)). The investigators reporting these results concluded that the expected age-dependent decline in these factors seen in ad-lib controls was somehow "delayed" by CR. According to the present invention, the interpretation of these results is that LFFAs are elevated in CR animals, and that these factors play a causal role in the beneficial effects associated with CR. Conversely, these factors are markedly reduced in anabolic states. In terms of caloric intake, in the wild, anabolic states would correspond to times of plenty and in the laboratory to ad-lib fed controls. Therefore, rather than being a mere consequence of catabolic events, LFFA are proposed to mediate the positive effects of CR.

Figure 2B:
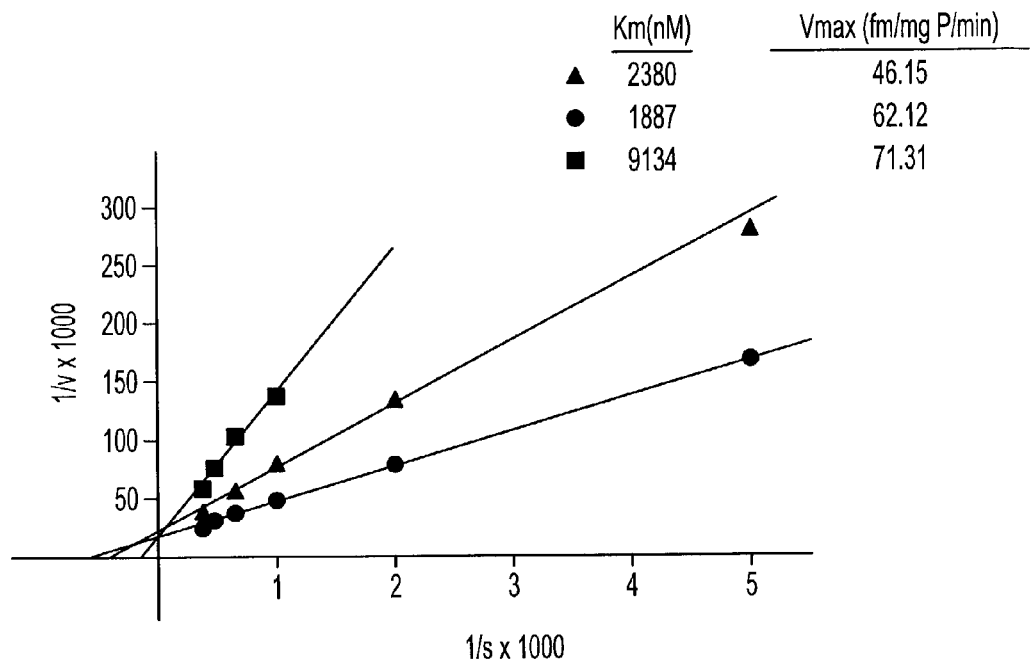
Figure 3B:
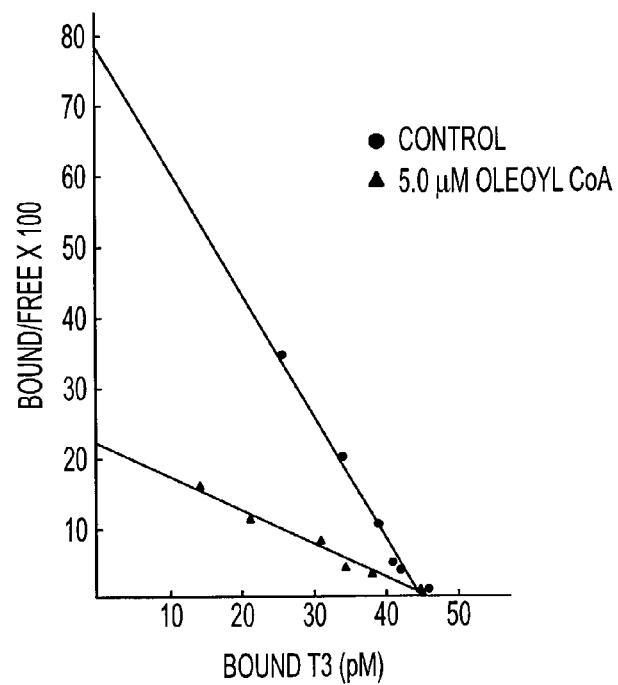

2) The control of metabolic rate (the regulation of energy utilization, calorigenesis and oxygen consumption) are regulated by thyroid hormones in homeotherms (Guyton, A C., "Medical Physiology", W. B. Saunders Co., Fifth Edition 1005 (1976)). Decreased thyroid hormone levels have been reported during starvation (Portray, G I, et al., *J. Clin Endocr. Metab.* 39:191-194 (1974)) and fasting (Vagenakis, A G., et al. *J. Clin Endocr. Metab.* 41:191-194 (1975)) in humans. Similarly, decreased thyroid hormone levels (Ingram, D K., et al., 1991) and lower core body temperature have been reported in rodents (Weindruch, R. H., et al., *Fed. Proc.* 38:2007-2016 (1979) and in primates (Lane, M A., et al., *Proc. Nat. Acad. Sci* 93:4159-4164 (1996)) subjected to CR. The inventor has concluded that elevated LFFA and CoALFFA are mediators of the beneficial effects of CR based on his previous studies demonstrating that these factors inhibit thyroid hormone synthesis (Chac∴n, M A., Doctoral Dissertation, Univ. of MD Graduate School (1985)), (see FIG. 2); and thyroid hormone receptor binding in vitro (FIG.

3). These hypotheses were subsequently confirmed by several laboratories (Wiersinga, W M, et al. *Metabolism* 37:996-1002 (1988), Fiona, R M., et al., *Bioch. Biophys. Res Comm.* 179-1011-1016 (1991), Li Q., et al., *J. Biochem.* 107-:699-702 9(1990), Li Q., et al., *J of Cell Biochem* 51:458-464 (1993)). In addition, decreased thyroid hormone levels have been associated with elevated LFFA in patients suffering from catabolic stresses of multiple etiologies (non-thyroidal illnesses), (Chopra, I J., et al., *J. Clin. Endocr. Metab.* 58:619-628 (1984), Chopra, I J., et al., *J. Clin. Endocr. Metab* 60:666-672 (1985), Chopra, I J., et al., *J. Clin. Endocr. Metab.* 60:980-984 (1985)). In CR, blocking of thyroid hormone expression by LFFAs and CoALFFAs would result in the conservation of limited energy fuels and a reduction in oxygen consumption. In turn, there would be a corresponding reduction in the formation of harmful oxygen radicals which have been implicated in the pathophysiology of human disease and aging (Yu, B P. (1993) "Free Radicals in Aging," CRC Press).

3) Decreased thyroid hormone levels and hypothermia are a consequence of CR (Ingram, D K., et al. (1991), Weindruch, R H., et al., (1979), Lane, M A., et al., (1996)). As proposed by Hochachka (*Science* 231:234-241 (1986)), hypoxia-tolerant animals can sustain prolonged hypothermia by metabolic arrest and stabilized membrane functions. Inhibition of high energy ion channels (ATPases) may be coupled to lower metabolic need for ATP as a means to cope with limited energy substrates and low oxygen conditions.

A variety of important biological processes are mediated by the active transport of ions across membranes. These include: protein biosynthesis, energy metabolism and maintenance of action potentials across membranes. The active ion transport includes transport of Na, K, and Ca ions by transmembrane ATPases.

(I) Sodium-Potassium ATPase is a high energy requiring enzyme which maintains high K and low Na inside the cell against a concentration gradient. In terms of energy metabolism, this ion gradient permits the incorporation of glucose into cells and intracellular potassium is required for maximal activity of pyruvate kinase. Na,K ATPase has been reported to be inhibited by free fatty acids (Kelly, R A., et al., *J. Biol. Chem.*, 261:11704-11711 (1986)). In the CR model of this invention, inhibition of Na,K ATPase by LFFAs would represent a net saving in energy (ATP) consumption but could also mediate other beneficial effects of CR.

(II) Calcium signals are involved in a variety of biological functions including secretory processes, muscle contraction, signal transduction, cell growth and the ability of cells to enter the cell cycle (Patterson, R L., et al., *Cell* 98:487-499 (1999), Berridge, M J., et al., *Nature* 395:645-648 (1998)). Intracellular calcium balance is maintained by Ca ATPase, an energy requiring transporter located in the sarcoplasmic/endoplasmic reticulum of cells (McLennan, D H., et al. *Ann N. Y Acad. Sci.* 671:1-10 (1992), Waldron, R T., et al., *J. Biol. Chem* 269:11927-11933 (1996)). Recent investigations have demonstrated a regulatory role of LFFA (Graber, M N., et al., *J. Biol Chem.* 271:883-888 (1996)) and CoALFFA (Rys-Sikora, K E., et al. *J. Biol. Chem* 269:31607-31613 (1994)) on Ca pools resulting in cell cycle activation. Extending these observations to the CR model, inhibition of Ca ATPase by LFFA and CoALFFA could result in energy conservation and a consequent rapid recovery from disease or injury that would contribute to a slowing of the aging process.

4) Serious exercise programs, such as those experienced by long distance runners and other similarly trained athletes, have been shown to decrease or to delay the onset of certain illnesses in humans (Hoffman-Goetz, L., "Excercise and Immune Function", CRC Press (1996)). In terms of energy metabolism, one would expect similar changes as those observed in CR animal models (lower glucose, lower insulin-glucagon ratios, etc.). It is interesting to observe that the levels of thyroid hormones are reduced (O'Connell, M., et al., *J. Clin Endocr. Metab.* 49:242-246 (1979)) and the levels of LFFAs are elevated as a consequence of prolonged exercise in humans (Opstad, P K., et al., *Clin. Endocr.* 20:657-669 (1984), as well as in rats (Lefebvre, P J., *Israel J. Med Sci.* 8:390-398 (1972)), which is consistent with the observations in CR animal models.

5) The increase in the number of centenarians in industrialized societies has experienced a phenomenal increase over the last two decades, a development attributed to disease prevention and improved health care. However, it is intriguing that the apparent increase in life span is also coincident with the high consumption of vegetable oils (olive oil, canola oil, and avocado) which are rich in oleic, linoleic, linolenic and palmitic acids, which have been reported to be elevated in CR models.

6) LFFA are elevated in neonates and infants (Williamson, D H., et al., *Dev. Neurosci.* 15:156-164 (1993), Girard, J R., et al. *Biochem. Soc. Transact.* 9:344-345 (1981)) as well as the elderly. These stages of life are also characterized by hypoxia tolerance (Haddad, G G., et al., *Annual Rev. Physiol.* 436: 629 (1984)) and reduced incidence of disease in the former and slower progression of disease in the later.

Mimicking Effects of Caloric Restriction

In keeping with the rationale set forth above, the present invention provides therapeutic interventions which mimics the effects of CR. This is achieved by introducing LFFAs and/or derivatives thereof (FACTORS) into mammals so that these FACTORS are present systemically at levels having biological effects comparable to the LFFA levels generated during CR. Alternatively, therapeutic intervention may be given which results in endogenous release of LFFAs from tissue stores. By achieving systemic levels of these FACTORS which compare with the levels generated during CR, the stress/protective responses are activated, with concomitant benefits for the organism.

The FACTORS

According to the method of this invention, one or more compounds (FACTORS) are administered to a mammal to achieve a systemic level which serves to provide the mammal with a signal equivalent to that experienced during CR. Suitable compounds include the LFFA (palmitic, oleic, linoleic, and linolenic acids), as well as the CoA adducts of these fatty acids (CoALFFA). In addition, analogs of these fatty acids which perform the same signaling function may be used. Such analogs will meet one or more of the in vitro and in vivo tests described in the Examples for evaluating FACTORS. Suitable analogs may be selected from the metabolic products of LFFA (gamma-linolenic acid (18:3n6), dihomo-gammalinolenic acid (20:3n6), arachidonic acid (20:4n6), eicosapentaenoic acid (20:5n3), docosahexaenoic acid (22:6n3), as well as fatty acids designated 18:4n3, 20:4n3, 22:4n6, 22:5n3, and 22:5n6, see, e.g., Stewart, et al., U.S. Pat. No. 4,826,877), non-hydrolyzable CoA analogs, such as S-(2-oxoalkyl)-CoA, where alkyl may be from 14-22 carbons, exemplified by S-(2-oxopentadecyl)-CoA), esters of the fatty acids and LFFA analogs (including alkyl esters, especially C1-3 alkyl, glycerol mono-, di-, and tri-esters, phosphoglycerol esters, etc.), or derivatives of LFFA which have greater stability and/or half-life in the circulatory system (e.g., reaction products which limit the reactivity of the unsaturated bonds in the aliphatic chain of the fatty acid without changing the configuration of the chain in regions critical to signaling). In addition, compounds including β-adrenergic agonists, e.g., isoproterenol, as well as direct effectors of hormone sensitive lipase (these may include small molecule activators as well as inhibitors of metabolism of the enzyme or other materials which preserve or enhance in vivo activity of the enzyme) may be used.

Administration of the Components

Therapeutic compounds according to this invention are preferably formulated in pharmaceutical compositions containing the compound and a pharmaceutically acceptable carrier. The pharmaceutical composition may contain other components so long as the other components do not reduce the effectiveness of the compound according to this invention so much that the therapy is negated. Pharmaceutically acceptable carriers are well known, and one skilled in the pharmaceutical art can easily select carriers suitable for particular routes of administration (Remington's Pharmaceutical Sciences, Mack Publishing Co., Easton, Pa., 1985).

The pharmaceutical compositions containing any of the compounds of this invention may be administered by parenteral (subcutaneously, intramuscularly, intravenously, intraperitoneally, intrapleurally, intravesicularly or intrathecally), topical, oral, rectal, or nasal route, as necessitated by choice of drug. The concentrations of the active agent in pharmaceutically acceptable carriers may range from 0.01 mM to 1 M or higher, so long as the concentration does not exceed an acceptable level of toxicity at the point of administration. The dose used in a particular formulation or application will be determined by the requirements of the particular type of disease and the constraints imposed by the characteristics and capacities of the carrier materials.

Dose and duration of therapy will depend on a variety of factors, including therapeutic index of the drug(s), as well as the subject's condition, age, weight, and tolerance of toxicity. Dose will generally be chosen to achieve serum concentrations from about 0.2 mM to about 2 mM. Preferably, initial dose levels will be selected based on their ability to achieve ambient concentrations shown to be effective in in vitro and in vivo models, such as those described herein, and in clinical trials, up to maximum tolerated levels. Typically, the dose will be selected to achieve a systemic increase in circulating LFFA of from 1.5× to 5×, or an equivalent level of another signaling compound. The dose of a particular drug and duration of therapy for a particular subject can be determined by the skilled clinician using standard pharmacological approaches in view of the above factors. The response to treatment may be monitored by analysis of blood or body fluid levels of the compound according to this invention, measurement of activity of the compound or its levels in relevant tissues or other clinical parameters based on standard monitoring techniques for determining the physiological state of the subject. For example, serum levels of LFFA may be quantitated by thin layer chromatography, Gas chromatography-mass spectroscopy, and/or high pressure liquid chromatography. Other relevant parameters include body temperature, metabolic rate (which may be determined by calorimetry), and thyroid hormone level (i.e., T3, which may be determined by radioimmunoassay, ELISA, etc.), as well as lowering of Na—K ATPase in blood cells. The skilled clinician will adjust the dose and duration of therapy based on the response to treatment revealed by these measurements.

A particularly preferred formulation for compounds according to this invention is in liposomes. Liposomes containing compounds according to this invention may be prepared by any of the methods known in the art for preparation of liposomes containing inclusions. Liposomes that are particularly suited for aerosol application to the lungs are described in International Patent Publication WO 93/12756, pages 25-29, incorporated herein by reference.

The compositions described above may be combined or used together or in coordination with another therapeutic substance.

Indications for this Method

The method of this invention applies generally to mammals, including livestock and household pets, and especially humans. The general population are candidates for therapy according to this invention for delay of the onset of aging and aging related disease. Chronic administration of one or more compounds according to this invention to individuals with no identified disease syndrome or health problem is within the contemplation of this invention. The method of this invention may also be beneficial to certain disease states in which the use of LFFA and derivatives is not counterindicated. Preferably, the method of this invention may be used to activate the stress/protective effect in any mammal in need thereof.

Surgical candidates may be treated prior to surgery by an acute course of therapy according to this invention to activate the stress/protective response. Typically, such administration will be initiated before surgery and will continue until the desired systemic level of the signaling molecules is achieved and/or until the stress/protective response is activated, as demonstrated by one or more of the responses discussed above, such as body temperature, metabolic rate, thyroid hormone levels or Na—K ATPase activity. The described intervention may also be used during surgery concomitantly with current methods for extracorporeal circulation (i.e., heart-lung machines) in order to achieve metabolic arrest and reduced oxygen consumption without need for the excessive chilling currently used in open-heart and neurosurgical procedures.

Similarly, activation of the stress/protective response in the absence of an identifiable disease state may be of value for soldiers or athletes who can anticipate traumatic injuries in the ordinary course of their expected activities. Administration of FACTORS according to this. invention may be beneficial for animals (including humans) which are (or are expected to be) exposed to hypoxia. Administration of factors in an amount sufficient to induce a stress/protective response provides some degree of protection against adverse effects of hypoxia, and therefore the invention contemplates treatment for situations involving high altitude, undersea, or outerspace operations, or in the clinics for conditions associated with acute or chronic hypoxia, such as angina, cerebrovascular, myocardial or peripheral vascular insults, pulmonary embolism or heart failure.

Finally, the beneficial effects of FACTORS in inducing protection and regeneration may also be apparent when applied locally. Therefore, topical application of FACTORS may have a cosmetic or anti-wrinkling effect in humans.

EXAMPLES

Example I

Testing the Effect of FACTORS on Biochemical Parameters in vitro

Numerous physiological systems are affected by the compounds which mediate the CR response. Certain of these systems may be isolated and observed in vitro, and these systems provide in vitro methods for demonstrating the effect of known FACTORS or confirming the activity of previously unknown FACTORS. The values obtained in the presence and absence of FACTORS will be determined, and the value for a candidate FACTOR may be compared to the value for LFFA or LFFACoA.

1. Thyroid hormone receptor binding will be performed as described by Li, et al., (Li Q., et al., *J. Biochem.* 107:699-702 (1990), Li Q., et al., *J of Cell Biochem* 51:458-464 (1993)) using purified liver receptor protein derived from Ad Lib fed rats. Binding of $^{125}$I-T3 to its receptor protein is measured in the presence of 5-50 μM candidate FACTORS. FACTORS will inhibit binding of T-3 to its receptor.

2. Na/K ATPase activity will be performed in the presence and absence of FACTOR using commercially available enzyme as described by Kelly, R A., et al., *J. Biol. Chem.*, 261:11704-11711 (1986). FACTORS will inhibit the hydrolysis of [γ-$^{32}$P] ATP and/or [$^3$H]-ouabain binding to Na—K ATPase.

3. Ca ATPase activity will be performed in the presence and absence of FACTOR using DDTIMF2 cells in culture (Rys-Sikora, K E., et al., *J. Biol. Chem.* 269:31607-31613 (1994)). FACTORS will inhibit GTP-activated $Ca^{2+}$-release by saponin-permeabilized cells.

4. Effect of FACTORS on the induction of protective genes (e.g., p53, SOD, α-2-globulin, HSP-70) may be determined by comparing the expression of protective genes in isolated hepatocytes incubated in the presence and absence of the FACTOR or candidate FACTOR. Expression will be increased in the presence of FACTORS such as LFFA, and demonstration of an increase in expression of these protective genes indicates that the candidates are indeed FACTORS or analogs of FACTORS. Gene induction may be quantified by Northern Analysis, RTPCR (Heydari, A R., et al., *Annals N.Y. Academy Science* 663:384-395 (1992)) and/or by oligonucleotide microarray (Lee, C., et al., *Science* 285:1390-1393 (1999)).

Example II

Testing the Effect of (FACTORS) on Biochemical Parameters in vivo

To further confirm the results of in vitro tests (Example 1) or for use as independent screening assays for candidate FACTORS, biochemical parameters and genetic markers, as well as indices of metabolism, will be compared in rodent populations either fed (i) ad lib, (ii) calorie restricted or (iii) ad lib but treated with experimental (candidate) factors. Animals will be treated for approximately three months. During the treatment period, the following tests will be performed.

1. Core body temperature will be performed weekly (Lane, M A., et al., *Proc. Nat. Acad. Sci.* 93:4159-4164 (1996)).

2. Indirect calorimetry ($O_2$ consumption) will be performed weekly (Lane, et al., 1996).

3. Biochemical studies (thyroid hormone binding, Na/K and Ca ATPase activity) will be performed using tissues of animals sacrificed at the beginning, middle (45 days) and end (90 days) of the study (Li Q., et al., *J. Biochem.* 107:699-702 (1990), Li Q., et al., *J of Cell Biochem* 51:458-464 (1993), Kelly, R A., et al., *J. Biol. Chem.*, 261:11704-11711 (1986), Rys-Sikora, K E., et al., *J. Biol. Chem.* 269:31607-31613 (1994)).

4. Protective gene induction will also be performed on animals sacrificed as in preceding paragraph 3 (Heydari, A R., et al., *Annals N.Y. Academy Science* 663:384-395 (1992); Lee, C., et al., Science 285:1390-1393 (1999)).

Example III

Demonstration of Delay in the Onset of Age-Associated Pathologies and/or Lengthened Longevity in Mammals 1. Delay of the onset of pathologies may be demonstrated for the age-related incidence of cancer in a susceptible animal model. A cancer susceptible strain of mice (p53 knockout) will be used for these studies (Perkins, S. N., et al., *Carcinogenesis* 18: 989-994 (1997); Hursting, S. D., et al., *Proc. Natl. Acad. Sci.* 91: 7036-7040 (1994). The incidence of tumors will be monitored in groups of mice fed ad lib, calorie restricted or fed ad lib but treated with factors.

2. Life span will be determined in groups of rats fed ad lib, calorie restricted or fed ad lib/treated with factors.

Example IV

Studies of the Effects of FACTORS on Other Disease or Physiological States

The effects of FACTORS and analogs of FACTORS may be tested in the following systems.

1. Hypoxia tolerance will be tested in ad lib fed rats as described by Haddad (Haddad, G G., et al., *Annual Rev. Physiol.* 46:629 (1984)) +/–factors.

2. Preoperative protection will be tested by subjecting ad lib fed rats +/–factors to a surgical procedure and establishing the rate of recovery (monitoring clinical and/or functional parameters relevant to the surgery). Surgical procedures include: A. Renal model of Ischemia—reperfussion (Bonventre, J. V., *Ann. Rev. Med.* 39: 531-544 (1988)) and B. Sciatic nerve crush injury (Wang, M. S., et al., *J. Pharmacol. Exp. Therapeut.*, 282: 1083-1093 (1997)).

3. Effect of factors on angiogenesis will be tested using the Matrigel Angiogenesis model in C57 mice (Passaniti, A., et al., *Lab. Invest.* 67: 519-528 (1992)).

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description is intended to illustrate, but not limit the scope of the invention. Modifications of the above-described modes for carrying out the invention that are apparent to persons of skill in medicine, immunology, nutrition, endocrinology, pharmacology, and/or related fields are intended to be within the scope of the invention, which is limited only by the appended claims.

All publications and patent applications mentioned in this specification are indicative of the level of skill of those skilled in the art to which this invention pertains. All publications and patent applications mentioned above are herein incorporated by reference to the same extent as if each individual publication or patent application was specifically and individually indicated to be incorporated by reference.

The invention claimed is:

1. A method of enhancing tolerance of hypoxia associated with surgery comprising:
    (a) selecting a mammal who is a surgical candidate,
    (b) administering a long chain free fatty acid CoA to said mammal prior to surgery by an acute course of therapy, wherein said long chain free fatty acid CoA is palmitoyl CoA in an amount sufficient to achieve a systemic level which serves to provide said mammal with a signal equivalent to that experienced during caloric restriction, and (c) whereby hypoxia tolerance is enhanced due to reduction in oxygen consumption.

2. A method of enhancing tolerance of hypoxia associated with surgery comprising:

(a) selecting a mammal who is a surgical candidate, (b) administering a long chain free fatty acid CoA to said mammal prior to surgery by an acute course of therapy, wherein said long chain free fatty acid CoA in an amount sufficient to achieve a systemic level which serves to provide said mammal with a signal equivalent to that experienced during caloric restriction, and (c) whereby hypoxia tolerance is enhanced due to reduction in oxygen consumption.

3. A method of enhancing tolerance of hypoxia associated with surgery comprising:

(a) selecting a mammal who is a surgical candidate, (b) administering a long chain free fatty acid CoA to said mammal prior to surgery by an acute course of therapy wherein said long chain free fatty acid CoA is linoleoyl CoA, in an amount sufficient to achieve a systemic level which serves to provide said mammal with a signal equivalent to that experienced during caloric restriction, and (c) whereby hypoxia tolerance is enhanced due to reduction in oxygen consumption.

\* \* \* \* \*

UNITED STATES PATENT AND TRADEMARK OFFICE
CERTIFICATE OF CORRECTION

PATENT NO. : 7,414,077 B2  Page 1 of 1
APPLICATION NO. : 10/120362
DATED : August 19, 2008
INVENTOR(S) : Marco Chacon It is certified that error appears in the above-identified patent and that said Letters Patent is hereby corrected as shown below:

Col. 11
Insert --is oleoyl CoA,-- in claim 2, line 6 under subsection (b) after "long chain free fatty acid CoA".

Signed and Sealed this

Eighth Day of September, 2009

David J. Kappos
*Director of the United States Patent and Trademark Office*

UNITED STATES PATENT AND TRADEMARK OFFICE
CERTIFICATE OF CORRECTION

PATENT NO. : 7,414,077 B2  Page 1 of 1
APPLICATION NO. : 10/120362
DATED : August 19, 2008
INVENTOR(S) : Marco Chacon It is certified that error appears in the above-identified patent and that said Letters Patent is hereby corrected as shown below:

Col. 11
Insert --is oleoyl CoA,-- in claim 2, line 10, after "long chain free fatty acid CoA".

This certificate supersedes the Certificate of Correction issued September 8, 2009.

Signed and Sealed this

Twenty-ninth Day of September, 2009

David J. Kappos
*Director of the United States Patent and Trademark Office*